US00PP09612P

United States Patent [19]

Zary

[11] Patent Number: Plant 9,612

[45] Date of Patent: Jul. 30, 1996

[54] CLIMBING MINIATURE ROSE PLANT NAMED 'JACMIPCL'

[75] Inventor: Keith W. Zary, Thousand Oaks, Calif.

[73] Assignee: Bear Creek Gardens, Inc., Medford, Oreg.

[21] Appl. No.: 491,105

[22] Filed: Jun. 16, 1995

[51] Int. Cl.[6] ..... A01H 5/00

[52] U.S. Cl. ..... Plt./5

[58] Field of Search ..... Plt./5, 9

[56] References Cited

U.S. PATENT DOCUMENTS

P.P. 6,011 9/1987 Warriner ..... Plt./9

*Primary Examiner*—Howard J. Locker

*Attorney, Agent, or Firm*—Klarquist Sparkman Campbell Leigh & Whinston, LLP

[57] ABSTRACT

A new rose variety of the climbing miniature class having a vigorous, arching habit of growth, small, pink, well-formed flowers; dark green, glossy, small leaves; resistance to rust and mildew; and an ability to have lateral buds break quickly and force new flowering shoots.

1 Drawing Sheet

The present invention relates to a new and distinct variety of rose plant of the climbing miniature class which was originated by me by crossing the variety JACship, U.S. Plant Pat. No. 7,948, with the an unnamed seedling (not patented).

The primary objective of this breeding was to produce a new rose variety having the attractive flower form and vigor of the female combined with the long arching canes, disease resistance and ability to have lateral buds break quickly into new flowering stems of the unnamed red flowered male seedling. The objective was substantially achieved, along with other desirable improvements, as evidenced by the following unique combination of characteristics that are outstanding in the new variety and that distinguish it from its parents, as well as from all other varieties of which I am aware:

1. Vigorous, arching growth habit.
2. Attractive, well-formed small pink buds produced in clusters.
3. Ability to have lateral buds break and form flowering shoots.
4. Resistant to both rose rust and powdery mildew.
5. Small, dark green, glossy foliage.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly ture as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—JACship, U.S. Plant Pat. No. 7,948.

*Pollen parent.*—Unnamed seedling (not patented).

Classification:

*Botanical.*—Rosa hybrida.

*Commercial.*—Climbing miniature.

FLOWER

Observations made from specimens grown in a garden environment at Somis, in Calif.

Blooming habit: Continuous.

Bud:

*Size.*—½-inch long when the petals start to unfurl.

*Form.*—The bud form is short and pointed ovoid.

*Color.*—When sepals first divide, bud color is Red Group 38A. When half blown, the upper sides of the petals are Red Group 38B; and the lower sides of the petals are Red Group 38A.

*Sepals.*—Color: Green Group 139C. Surface texture: Covered in fine hairs. There are three lightly appendaged sepals. There are two unappendaged sepals with hairy edges.

*Receptacle.*—Color Green Group 137D. Shape: Funnel. Size: Small (3/16×3/16"). Surface: Smooth.

*Peduncle.*—Length: Short (¾ inch). Surface: Glandular. Color: Medium-green. Strength: Stiff, erect and slender.

Bloom:

*Size.*—Small. Average open size is 1½ inches.

*Borne.*—Several together in pyramidal to rounded clusters of 3–7 flowers.

*Stems.*—Strong and long (up to 3 feet).

*Form.*—When first open: High centered. Permanence: Flattens and outer petals curl back.

*Petalage.*—Number of petals under normal conditions: 20.

*Color.*—The upper side of the petals is Red Group 38B. The reverse side of the petals is Red Group 39A. The base of each petal has a yellow half-moon at its point of attachment. The major color on the upper side is Red Group 38B.

*Variegations.*—None.

*Discoloration.*—The general tonality at the end of the first day: No change. At the end of the third day: No change.

*Fragrance.*—Slight.

Petals:

*Texture.*—Thick.

*Shape.*—Deltoid.

*Form.*—Tips slightly recurved and edges slightly quilled.

*Arrangement.*—Imbricated, with few petaloids in the center.

*Persistence.*—Drop off cleanly.

*Lastingness.*—On the plant: Fair (5–7 days). As a cut flower: Fair (6–8 days).

Reproductive parts:

*Anthers.*—Size: Medium. Quantity: Many. Color: Yellow. Arrangement: Regular around styles.

*Filaments: Color: Yellow.*

*Pollen.*—Color Gold yellow.

*Styles.*—Color: Red.

*Stigmas.*—Color: Red.

Form: Climber.

Growth: Very vigorous and upright; as it flowers, it arches over, with lateral buds breaking freely and flowering. The plant will reach 6 feet in height and 4 feet in width in one year.

Foliage:

*Number of leaflets on normal mid -stem leaves.*—5 or 7.

*Size.*—Small (3"×2").

*Quantity.*—Abundant.

*Color.*—New foliage: Greyed Orange 176A, but turns green quickly. Old foliage: Upper surface: Green Group 139A; Lower surface: Green Group 139B.

Leaflets:

*Shape.*—Pointed oval.

*Texture.*—Upper side: Leathery and glossy.

*Edge.*—Serrated.

*Serration.*—Single and small.

*Petiole rachis.*—Color: Green.

*Petiole underside.*—Rough, with prickles.

*Stipules.*—Short (⅜"), serrated and bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Many. On laterals from main canes: Many.

*Form.*—Short (⅛"), hooked slightly downward.

*Color when young.*—Red.

Small prickles:

*Quantity.*—On main stalks: Few. On laterals: Few.

*Color.*—Brown when old; red when young.

I claim:

1. A new and distinct variety of rose plant of the climbing miniature class, substantially as herein shown and described, characterized particularly as to novelty by the unique combination of its vigorous arching habit of growth, its small, pink, well-formed flowers, its dark green, glossy, small leaves, its resistance to rust and mildew and its ability to have lateral buds break quickly and force new flowering shoots.

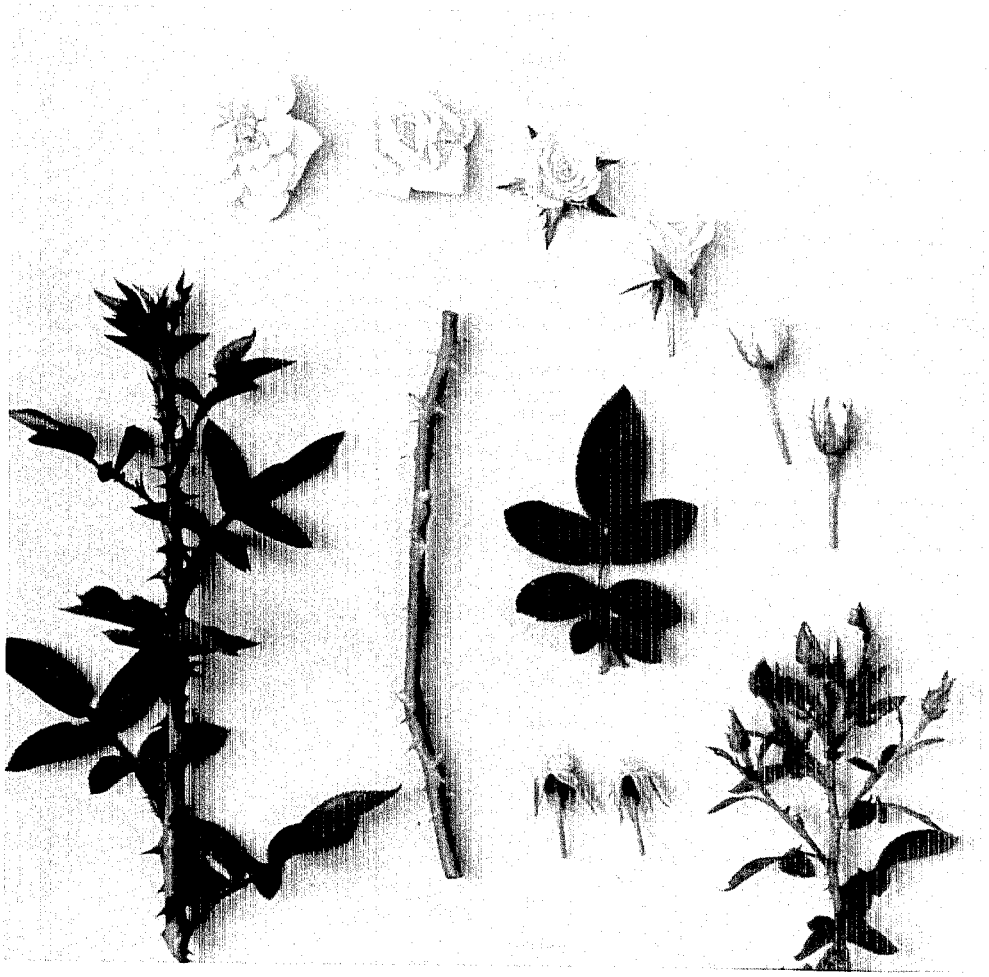

* * * * *